US011395810B2

(12) United States Patent
Kamphuis et al.

(10) Patent No.: US 11,395,810 B2
(45) Date of Patent: *Jul. 26, 2022

(54) MEMORY IN SUBJECTS WITH MINI-MENTAL STATE EXAMINATION OF 24-26

(71) Applicant: N.V. NUTRICIA, HM Zoetermeer (NL)

(72) Inventors: Patrick Joseph Gerardus Hendrikus Kamphuis, Utrecht (NL); Martine Groenendijk, Barendrecht (NL); Anke Bongers, Veenendaal (NL)

(73) Assignee: N.V. Nutricia, Zoetermeer (NL)

( * ) Notice: Subject to any disclaimer, the term of this patent is extended or adjusted under 35 U.S.C. 154(b) by 64 days.

This patent is subject to a terminal disclaimer.

(21) Appl. No.: 16/696,941

(22) Filed: Nov. 26, 2019

(65) Prior Publication Data

US 2020/0197345 A1 Jun. 25, 2020

Related U.S. Application Data

(63) Continuation of application No. 12/666,611, filed as application No. PCT/NL2008/050411 on Jun. 20, 2008, now abandoned.

(30) Foreign Application Priority Data

| Jun. 27, 2007 | (WO) | PCT/NL2007/050306 |
| Jun. 27, 2007 | (WO) | PCT/NL2007/050307 |
| Jun. 27, 2007 | (WO) | PCT/NL2007/050310 |
| Dec. 20, 2007 | (EP) | 07123811 |
| Mar. 4, 2008 | (WO) | PCT/NL2008/050124 |

(51) Int. Cl.
*A61K 31/202* (2006.01)
*A61K 31/7072* (2006.01)
*A61K 45/06* (2006.01)
*A61K 31/14* (2006.01)
*A23L 33/00* (2016.01)
*A61P 25/28* (2006.01)
*A61K 31/557* (2006.01)
*A23L 33/16* (2016.01)
*A23L 33/12* (2016.01)
*A23L 33/15* (2016.01)
*A23L 33/10* (2016.01)

(52) U.S. Cl.
CPC ............ *A61K 31/202* (2013.01); *A23L 33/10* (2016.08); *A23L 33/12* (2016.08); *A23L 33/15* (2016.08); *A23L 33/16* (2016.08); *A23L 33/40* (2016.08); *A61K 31/14* (2013.01); *A61K 31/557* (2013.01); *A61K 31/7072* (2013.01); *A61K 45/06* (2013.01); *A61P 25/28* (2018.01); *A23V 2002/00* (2013.01)

(58) Field of Classification Search
CPC .... A61K 31/202; A61K 31/14; A61K 31/557; A61K 31/7072; A23L 33/12; A23L 33/13; A23L 33/15; A23L 33/40; A61P 25/28
See application file for complete search history.

(56) References Cited

U.S. PATENT DOCUMENTS

| 3,600,197 | A | 8/1971 | Spangler et al. |
| 5,378,488 | A | 1/1995 | Dimler et al. |
| 5,470,838 | A | 11/1995 | Von Borstel et al. |
| 5,886,037 | A | 3/1999 | Klor et al. |
| 6,316,426 | B1 | 11/2001 | Von Borstel et al. |
| 6,689,467 | B1 | 2/2004 | Joubert et al. |
| 6,835,750 | B1 | 12/2004 | Henderson |
| 7,090,879 | B2 | 8/2006 | Albrecht et al. |
| 8,282,335 | B2 | 10/2012 | Bark |
| 8,282,965 | B2 | 10/2012 | De Kort et al. |
| 8,283,335 | B2 | 10/2012 | Hageman et al. |
| 8,283,336 | B2 | 10/2012 | Groenendijk et al. |
| 8,361,989 | B2 | 1/2013 | Groenendijk et al. |
| 8,759,319 | B2 | 6/2014 | Hageman et al. |
| 8,791,089 | B2 | 7/2014 | Groenendijk et al. |
| 9,132,196 | B2 | 9/2015 | De Kort et al. |
| 2003/0114415 | A1 | 6/2003 | Wurtman et al. |
| 2004/0001817 | A1 | 1/2004 | Giampapa |
| 2005/0208179 | A1 | 9/2005 | Albrecht et al. |
| 2006/0025376 | A1 | 2/2006 | Wurtman |
| 2006/0241077 | A1 | 10/2006 | Wurtman et al. |
| 2007/0004670 | A1 | 1/2007 | Wurtman et al. |
| 2007/0140992 | A1 | 6/2007 | Schick et al. |
| 2010/0323982 | A1 | 12/2010 | Hageman et al. |
| 2010/0331258 | A1 | 12/2010 | Kamphuis et al. |
| 2010/0331275 | A1 | 12/2010 | Groenendijk et al. |
| 2011/0006917 | A1 | 1/2011 | Taniguchi et al. |

(Continued)

FOREIGN PATENT DOCUMENTS

| EP | 0 175 468 A2 | 3/1986 |
| EP | 1 216 041 B1 | 2/2004 |

(Continued)

OTHER PUBLICATIONS

"Derivative—Definition and More from the Free Merriam-Webster Dictionary" Retrieved Oct. 22, 2012 from http/www.merriam-webster.com/dictionary/derivative.

(Continued)

*Primary Examiner* — Olga N Chernyshev
(74) *Attorney, Agent, or Firm* — N.V. Nederlandsch Octrooibureau

(57) ABSTRACT

The invention thus pertains to the use of a composition comprising: (a) uridine or uridine phosphate; and (b) docosahexaenoic acid and/or eicosapentaenoic acid, for improving memory and/or the treatment or prevention of impaired memory function, in a subject with a mini-mental state examination of 24-26, wherein said composition is enterally administered to the subject. In the MMSE test, any score of 27 or higher (out of 30) is effectively normal. In the patients with dementia, 20-26 indicates mild dementia, 10-19 moderate dementia, and below 10 severe dementia. It was the present inventors' belief that within the group of 20-26, the memory impairment in the sub-group of 24-26 may even be reversible, as the pathological pathways have just started to develop. In this group of subjects the pathological pathways have just started to develop. Clinical studies show excellent results for this subgroup.

10 Claims, No Drawings

(56) References Cited

U.S. PATENT DOCUMENTS

| | | | |
|---|---|---|---|
| 2011/0009357 | A1 | 1/2011 | Hageman et al. |
| 2011/0027391 | A1 | 2/2011 | De Kort et al. |
| 2011/0105594 | A1 | 5/2011 | De Kort et al. |
| 2013/0012469 | A1 | 1/2013 | De Kort et al. |
| 2013/0018012 | A1 | 1/2013 | Hageman et al. |

FOREIGN PATENT DOCUMENTS

| | | | |
|---|---|---|---|
| EP | 1 656 839 | A1 | 5/2006 |
| EP | 1 666 092 | A2 | 6/2006 |
| EP | 1 800 675 | A1 | 6/2007 |
| EP | 1 282 365 | B1 | 12/2007 |
| WO | WO-94/05319 | A1 | 3/1994 |
| WO | WO-00/38829 | A1 | 7/2000 |
| WO | WO-01/32034 | A1 | 5/2001 |
| WO | WO-01/82928 | | 11/2001 |
| WO | WO-02/088159 | A1 | 11/2002 |
| WO | WO-02/096464 | A1 | 12/2002 |
| WO | WO-03/013276 | A1 | 2/2003 |
| WO | WO-03/041701 | A2 | 5/2003 |
| WO | WO-2005/039597 | A2 | 5/2005 |
| WO | WO-2006/031683 | A2 | 3/2006 |
| WO | WO-2006/118665 | A2 | 11/2006 |
| WO | WO-2006/127620 | A1 | 11/2006 |
| WO | WO-2007/001883 | A2 | 1/2007 |
| WO | WO-2007/004685 | A2 | 1/2007 |
| WO | WO-2007/004689 | A1 | 1/2007 |
| WO | WO-2007/008586 | A2 | 1/2007 |
| WO | WO-2007/058538 | A2 | 5/2007 |
| WO | WO-2007/073178 | A2 | 6/2007 |
| WO | WO-2007/089703 | A2 | 8/2007 |
| WO | WO-2009/002145 | A1 | 12/2008 |
| WO | WO-2009/002146 | A1 | 12/2008 |
| WO | WO-2009/002148 | A1 | 12/2008 |
| WO | WO-2009/002163 | A1 | 12/2008 |
| WO | WO-2009/002164 | A1 | 12/2008 |
| WO | WO-2009/002165 | A1 | 12/2008 |
| WO | WO-2009/002166 | A1 | 12/2008 |
| WO | WO-2009/057994 | A1 | 5/2009 |
| WO | WO-2009/082203 | A1 | 7/2009 |
| WO | WO-2009/082227 | A1 | 7/2009 |
| WO | WO-2011/011721 | A2 | 1/2011 |

OTHER PUBLICATIONS

Albert, M. et al. "Preclinical prediction of AD using neuropsychological tests", Journal of the International Neuropsychological Society, 2001, vol. 7, pp. 631-639.
Baudic et al., "Executive function deficits in early Alzheimer's disease and their relations with episodic memory", Archives of Clinical Neuropsychology, 2006, vol. 21, pp. 15-21.
Beers et al., "Section 1; Nutritional Disorders; Chapter 1, Nutrition: General Considerations," The Merck Manual of Diagnosis and Therapy, 17th Edition, Merck & Co., Whitehouse Station, N.J., 1999, pp. 1-23.
Bird, T.D., Genetic aspects of Alzheimer disease, Genetics in Medicine, Apr. 2008, vol. 10, No. 4, p. 231-237.
Birenbaum et al., "Open-ended versus multiple-choice formats—it does make a difference for diagnostic purposes", Applied Psychological Measurement, Dec. 1987, vol. 11, No. 4, pp. 385-395.
Bowie et al, "Administration and interpretation of the Trail Making Test," Nature Protocols, 2006, vol. 1, No. 5, pp. 2277-2281.
Cansev, M. et al. "Chronic Administration of Docosahexaenoic Acid or Eicosapentaenoic Acid, But Not Arachidonic Acid, Alone or in Combination with Uridine, Increases Brain Phosphatide and Synaptic Protein Levels in Gerbils", Neuroscience, 2007, vol. 148, pp. 421-431.
Cansev, M. et al. "Oral administration of circulating precursors for membrane phosphatides can promote the synthesis of new brain synapses", Alzheimer's & Dementia, 2008, vol. 4, pp. S153-S168.
Cole, G. et al. "Docosahexaenoic Acid Protects From Amyloid and Dendritic Pathology In An Alzheimer's Disease Mouse Model", Nutrition and Health, 2006, vol. 18, pp. 249-259.
Cooper, et al. "The Clinical Assessment of the Patient with Early Dementia", J Neurol Neurosurg Psychiatry, 2005, vol. 76 (Suppl V.), v15-v24.
Cormier, et al. "Diet and Child Behavior Problems: Fact or Fiction?", Pediatric Nursing, Mar.-Apr. 2007, vol. 33, No. 2, pp. 138-143.
DeBruin et al., "Combined uridine and choline administration improves cognitive deficits in spontaneously hypertensive rats", Neurobiology of Memory and Learning, Jul. 2003, vol. 80, No. 1, pp. 63-79.
Decision Science News, "Recognition vs. Recall", Sep. 27, 2006, obtained from http://www.decisionsciencenews.com/2006/09/27/recognition-vs-recall/.
Diagnostic and Statistical Manual of Mental Disorders (fourth Edition, 2000) 013 DSM-IV-TR; American Psychiatric Association. (table of contents only).
Folstein, et al. "A Practical Method for Grading the Cognitive State of Patients for the Clinician", J. Psychiat. Res., 1975, vol. 12, pp. 189-198.
Freemantle, et al. "Omega-3 fatty acids, energy substrates, and brain function during aging", Prostaglandins Leukotrienes and Essential Fatty Acids, 2006, vol. 75, pp. 213-220.
Freund-Levi, Y. et al. "w-3 Fatty Acid Treatment in 174 Patients With Mild to Moderate Alzheimer Disease: OmegAD Study", Arch Neurol, Oct. 2006, vol. 63, pp. 1402-1408.
Garcia, et al. "Daily larval growth and RNA and DNA content of the NW Mediterranean anchovy *Engraulis encrasicolus* and their relations to the environment", Marine Ecology Progress Series, May 28, 1998, vol. 166, pp. 237-245.
Gluck, et al. "Psychobiolgical Models of Hippocampal Function in Learning and Memory", Neurobiology of Learning and Memory, Academic Press, 1998, Chapter 11, pp. 417-448.
Harrison, John et al., "A neuropsychological test battery for use in Alzheimer disease clinical trials", Archives of Neurology, vol. 64, No. 9, Sep. 2007, pp. 1323-1329.
Holguin, "Consuming a Diet Enriched with Choline, UMP, and DHA Improves Memory in Rodents when these Compounds Increase Phospholipids", Massachusetts Institute of Technology, published Mar. 5, 2008.
Holguin, et al. "Chronic administration of DHA and UMP improves the impaired memory of environmentally impoverished rats", Behavioural Brain Research, 2008, vol. 191, pp. 11-16.
Holguin, S. et al. "Chronic administration of DHA and UMP improves the impaired memory of environmentally impoverished rats", Behavioural Brain Research, 2008, vol. 191, pp. 11-16.
International Search Report dated Dec. 14, 2012 in PCT/NL2012/050753.
International Search Report dated Feb. 20, 2013 in PCT/NL2012/050754.
International Search Report dated Nov. 29, 2012 in PCT/NL2012/050751.
Kalmijn, et al. "Polyunsaturated Fatty Acids, Antioxidants, and Cognitive Function in Very Old Men", American Journal of Epidemiology, 1997, vol. 145, No. 1, pp. 33-41.
Katoku et al., "Nutrient Compositions Containing Nucleic Acid Related Compounds, used for Growth and Health Maintenance—Contain e.g. Docosahexaenoic Acid, Arachidonic Acid and Cholesterol" WPI/Thomson, Jan. 13, 1998, 1 page [XP002470089].
Kidd, "Omega-3 DHA and EPA for cognition, behavior, and mood: clinical findings and structural-functional synergies with cell membrane phospholipids", Alternative Medicine Review, 2007, vol. 12, No. 3, pp. 207-227.
Korezyn, A. et al. "The prevention of the dementia epidemic", Journal of the Neurological Sciences, 2007, vol. 257, pp. 2-4.
Lannfelt, et al. "Safety, efficacy, and biomarker findings of PBT2 in targeting Abeta as a modifying therapy for Alzheimer's disease: a phase IIa, double-blind, randomised, placebo-controlled trial" The Lancet Neurology, 2008, vol. 7, Issue 9, pp. 779-786.
Luchsinger, et al. "Dietary factors and Alzheimer's disease", The Lancet—Neurology, Oct. 2004, vol. 3, pp. 579-587.
Markesbery, W. et al. "Neuropathologic Substrate of Mild Cognitive Impairment", Arch Neurol, Jan. 2006, vol. 63, pp. 38-46.
Morris, J. "Mild Cognitive Impairment Is Early-Stage Alzheimer Disease", Arch Neurol., 2006, vol. 63, No. 1, 6 pgs.

(56) References Cited

OTHER PUBLICATIONS

Nitsch, R. et al. "Evidence for a membrane defect in Alzheimer disease brain", Proc. Natl. Acad. Sci., Mar. 1992, vol. 89, pp. 1671-1675.
Oksman, M. "Impact of different saturated fatty acid, polyunsaturated fatty acid and cholesterol containing diets on beta-amyloid accumulation in APP/PS1 transgenic mice", Neurobiology of Disease, 2006, vol. 23, pp. 563-572.
Purina Garden Recipe, http://purinasmallanimals.com/SmallAnimals/Gerbil/PurinaGardenRecipeGerbiland, retrieved Oct. 15, 2013, 4 pgs.
Quadri et al. "Homocysteine, folate, and vitamin B-12 in mild cognitive impairment, Alzheimer disease, and vascular dementia", Am. J. Clin. Nutr., 2004, vol. 80, pp. 114-122.
Rabin et. al., "Assessment practices of clinical neuropsychologists in the United States and Canada: A survey of INS, NAN, and APA Division 40 members", Archives of Clinical Neuropsychology, 2005, vol. 20, pp. 33-65.
Reynolds, E. "Vitamin B12, folic acid, and the nervous system", Review, Nov. 2006, vol. 5, pp. 949-960.
Richter et al., "Cognitex supplementation in elderly adults with memory complaints: an uncontrolled open label trial", Journal of Dietary Supplements, 2011, vol. 8, No. 2, pp. 158-168.
Sabin et al., "Citicoline in vascular cognitive impairment and vascular dementia after stroke", Stroke, 2011, vol. 42 [suppl 1], pp. S40-S43.
Sakamoto, T. et al. "Oral supplementation with docosahexaenoic acid and uridine-5'-monophosphate increases dendritic spine density in adult gerbil hippocampus", Brain Research, 2007, vol. 1182, pp. 50-59.
Scheff, et al. "Hippocampal synaptic loss in early Alzheimer's disease and mild cognitive impairment", Neurobiology of Aging, 2006, vol. 27, pp. 1372-1384.
Scheltens et al., "Efficacy of a medical food in mild Alzheimer's disease: A randomized controlled trial", Alzheimer's & Dementia (2010), vol. 6, No. 1, pp. 1-10.
Shah, et al. "The S-Connect study: results from a randomized, controlled trial of Souvenaid in mild-to-moderate Alzheimer's disease", Alzheimer's Research & Therapy, 2013, vol. 5, pp. 1-9.
Skinner et al., "The Alzheimer's Disease Assessment Scale-Cognitive-Plus (ADAS-Cog-Plus): an expansion of the ADAS-Cog to improve responsive in MCI," Brain Imaging Behav., Dec. 2012, vol. 6, No. 4, pp. 1-24.
Snyder, Peter J., "Assessment of cognition in mild cognitive impairment: A comparative study", Alzheimer's & Dementia: The Journal of the Alzheimer's Association, vol. 7, No. 3, Sep. 2007, pp. 338-355.
Stern et al., "Executive functioning", Chapter 13 in The Handbook of Alzheimer's Disease and Other Dementias, First edition, 2011, pp. 369-415.
Welsh, et al. "Detection of abnormal memory decline in mild cases of Alzheimer's disease using CERAD neuropsychological measures", Arch Neurol, Mar. 1991, vol. 48, No. 3, pp. 278-281, Abstract Only.
Westerburg et. al, "When memory does not fail: familiarity-based recognition in mild cognitive impairment and Alzheimer's Disease", Neuropsychology, 2006, vol. 20, No. 2, pp. 193-205.
Wood-Kaczmar et al. Understanding the molecular causes of Parkinson's disease, Trends in Molecular Medicine, vol. 12, No. 11 (2006), pp. 521-528.
Worley, "Odyssey: Why Do Our Brains Betray Us?—The Fight against Alzheimer's Intensifies", University of Kentucky, Spring 2004, pp. 1-17.
Wurtman et al., "Synaptic proteins and phospholipids are increased in gerbil brain by administering uridine plus docosahexaenoic acid orally", Brain Research, 2006, vol. 1088, pp. 83-92.
Wurtman, et al., Annals of the New York Academy of Sciences—The Neurobiology of Alzheimer's Disease, 1996, vol. 777.
U.S. Appl. No. 12/666,611, filed May 11, 2010, and PCT/NL2008/050411, filed Jun. 20, 2008.

MEMORY IN SUBJECTS WITH MINI-MENTAL STATE EXAMINATION OF 24-26

CROSS-REFERENCE TO RELATED APPLICATIONS

This application is a Continuation of U.S. patent application Ser. No. 12/666,611, filed May 11, 2010, which is a National Stage application of PCT/NL2008/050411, filed Jun. 20, 2008, which claims the benefit and priority of Patent Application PCT/NL2007/050306, filed Jun. 26, 2007; PCT/NL2007/050307, filed Jun. 26, 2007; PCT/NL2007/050310, filed Jun. 27, 2007; European Patent Application 07123811.7, filed Dec. 20, 2007 and PCT/NL2008/050124, filed Mar. 4, 2008. The foregoing applications are incorporated by reference herein in their entirety.

FIELD OF THE INVENTION

The invention relates to the use of a composition for improving memory function, in a subject with a mini-mental state examination of 24-26.

BACKGROUND OF THE INVENTION

Memory impairment is a serious shortcoming in many humans, particularly those suffering from Alzheimer's disease and/or elderly. Such impairments often have serious consequences, such as reduced quality of life, difficulties in performing the activities of daily living, potentially resulting in hospitalization or institutionalization.

Several treatments have been suggested for the improvement of memory function in subjects. However, very few have been proven effective. Moreover, the administration of several nutritional ingredients has also been suggested.

SUMMARY OF THE INVENTION

Nutritional therapy is particularly desired in subjects who have relatively mild symptoms of memory impairment, i.e. subjects with a mini-mental state examination score (MMSE) of 24 to 26. The present inventors have recognized that in this particular subgroup memory improvement has enormous effect for the subject activities of daily living and quality of life. This subgroup of subjects is distinct in that the pathological pathways have just started to develop. In the MMSE test, any score of 27 or higher (out of 30) is effectively normal. In the patients with dementia, 20-26 indicates mild dementia, 10-19 moderate dementia, and below 10 severe dementia. It was the present inventors' belief that within the group of 20-26, the memory impairment in the sub-group of 24-26 may even be reversible, as the pathological pathways have just started to develop. It would be highly desired to improve the memory function of this subgroup of subjects, as this may delay the need or reduce the dosage of treatment with pharmaceutical drugs. Moreover, improvements in subjects with a MMSE of 24 to 26 can postpone the need for a subject to be hospitalized or institutionalized, enable a longer independent living, improve the quality of life or improve the ability to perform daily activities.

The subgroup of subjects with a MMSE score of 24 to 26 comprises two populations. Firstly, it comprises those subjects who do not receive medication for memory impairment, i.e. the drug naïve subjects. The treatment of this subgroup is particularly preferred as in these subjects the balance between side effects and benefits of pharmaceutical intervention is still negative. Providing nutritional therapy to these subjects is desired because of the relative lack of negative side effects. For subjects with a MMSE of 24 to 26 who are drug naïve, it is particularly important to develop a therapy which delays the point in time where pharmaceutical drugs have to be administered.

Secondly, the subgroup of subjects with a MMSE score of 24 to 26 comprises a population of subjects with a very mild form of Alzheimer's Disease. Memory improvement through nutritional therapy is particularly desired in subjects with a very mild form of Alzheimer's Disease. If improvement of memory function could be achieved pharmaceutical intervention could be reduced or even postponed if significant improvements are observed.

It is however particularly difficult to find a (nutritional) composition which effectively improves memory function in the group with a MMSE of 24 to 26 as the pathological pathways have only started to develop and symptoms are very mild. Detecting differences between control and treatment group is particularly difficult, and hence effective treatment requires intensive testing.

The present inventors surprisingly found, through clinical study, that administration of a composition containing (a) uridine or uridine phosphate; and (b) docosahexaenoic acid and/or eicosapentaenoic acid showed a significant improvement of memory function in subjects with a MMSE of 24 to 26. Compliance and tolerability were very high and side effects were relatively low. It was particularly surprising that the present clinical data showed an actual improvement in memory function, more than just a reduction in the rate of decline in memory function. Additionally it was found that in this subgroup the delayed recall function was significantly improved. The results of the clinical study are summarized in the examples.

DETAILED DESCRIPTION OF THE INVENTION

The invention thus pertains to the use of a composition comprising:
a. uridine or uridine phosphate; and
b. docosahexaenoic acid and/or eicosapentaenoic acid
for improving memory and/or the treatment or prevention of impaired memory function, in a subject with a mini-mental state examination of 24-26, wherein said composition is enterally administered to the subject.

Subjects

The present invention relates to subjects with a mini-mental state examination of 24, 25 or 26, i.e. of 24-26. The mini-mental state examination (MMSE) is a brief 30-point questionnaire test that is used to assess cognition. In the time span of about 10 minutes it samples various functions including memory and orientation. The MMSE test includes simple questions and problems in a number of areas: the time and place of the test, repeating lists of words, language use and comprehension, and basic motor skills. Any score of 27 or higher (out of 30) is effectively normal; 20-26 indicates mild dementia; 10-19 moderate dementia, and below 10 severe dementia. The MMSE is a standardized test. Copyrights prevent the inventors from including a copy of the questionnaire into the specification, but it is readily accessible on the internet and available through copyright owner Psychological Assessment Resources (PAR). It is first introduced by Folstein et al. (Psych Res 12:189, 1975), and is widely used with small modifications to assess cognition.

The subjects as treated in the present invention have a mini-mental state examination score of 24-26 and are preferably drug naïve and/or suffer from a very mild form of Alzheimer's disease, preferably drug naïve subjects with a very mild Alzheimer's disease and a MMSE of 24-26. The term "drug naïve" as used in the present invention refers to subjects who do not ingest one or more of cholinesterase inhibitors, N-methyl-D-aspartate (NMDA) antagonists and *Ginkgo biloba*. In the clinical study presented here, it was found that the present composition is effective in drug naïve subjects. The subject is preferably a human, preferably an elderly human, preferably at least 50 years of age.

Memory

The present invention relates to use of the present composition for (i) the improvement of memory and/or (ii) treatment and/or prevention of impaired memory function. Alternatively, the present invention provides a method for (i) the improvement of memory and/or (ii) treatment and/or prevention of impaired memory function in a subject in need thereof, said method comprising the administration of the present composition to said subject. Particularly, the present invention relates to the treatment of an impaired memory function. It was found that the memory function actually improved when the present composition was administered to the subject. The memory function of a human subject can suitably be determined using the (modified) ADAS-cog, Wechsler Memory Scale, WMS revised.

It was particularly found that in these subjects the delayed recall function was improved. Delayed recall function can be measured by a prose recall task 30-minute delay interval. Delayed recall of a prose passage is not a measure to differentiate clearly between very mild dementia of the Alzheimer type and normal ageing. Hence, the present composition can also advantageously help subjects not (yet) suffering from Alzheimer's disease in improving the delayed recall function. Hence, in a preferred embodiment the invention provides a method for improving delayed recall and/or the treatment and/or prevention of an impaired delayed recall function.

Uridine

Preferably the present composition comprises uridine and/or uridine phosphate. Preferably the present composition comprises one or more uridine phosphates selected from uridine monophosphate (UMP), uridine diphosphate (UDP) and uridine triphosphate (UTP).

Most preferably the present composition comprises UMP. Preferably at least 50 wt. % of the uridine in the present composition is provided by UMP, more preferably at least 75 wt. %, most preferably at least 95 wt. %. The present method preferably comprises the administration of uridine (the cumulative amount of uridine, deoxyuridine, uridine phosphates, uracil and acylated uridine derivatives) in an amount of 0.08-3 g per day, preferably 0.1-2 g per day, more preferably 0.2-1 g per day. The present method preferably comprises the administration of a composition comprising uridine in an amount of 0.08-3 g UMP per 100 ml liquid product, preferably 0.1-2 g UMP per 100 ml liquid product, more preferably 0.2-1 g per 100 ml liquid product. Preferably 1-37.5 mg UMP per kilogram body weight is administered per day. The required dosages of the equivalents on a weight base can be calculated from the dose for UMP by taking equimolar amounts using the molecular weight of the equivalent and of UMP, the latter being 324 Dalton.

Docosahexaenoic Acid and/or Eicosapentaenoic Acid

The present composition preferably comprises at least docosahexaenoic acid (22:6 ω-3; DHA) and/or eicosapentaenoic acid (20:5 ω-3; EPA), preferably DHA and EPA. The DHA and/or EPA is preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form.

The present method preferably comprises the administration of 400-5000 mg (DHA+EPA) per day, more preferably 500-3000 mg per day, most preferably 1000-2500 mg per day. The proportion of (DHA+EPA) of the total fatty acids present in the composition is preferably 5-50 wt. %, more preferably 10-45 wt. %, most preferably 15-40 wt. %. The present method preferably comprises the administration of DHA, preferably in an amount of 300-4000 mg per day, more preferably 500-2500 mg per day.

The present composition preferably contains a very low amount of arachidonic acid (AA). Preferably the weight ratio DHA/AA in the present composition is at least 5, preferably at least 10, more preferably at least 15, preferably up to e.g. 60 or up to 30. The present method preferably comprises the administration of a composition comprising less than 5 wt. % arachidonic acid based on total fatty acids, more preferably below 2.5 wt. %, e.g. down to 0.5 wt %. The ratio omega-6/omega-3 fatty acids in the present product is preferably below 0.5, more preferably below 0.2, e.g. down to 0.05 or to 0.1. The ratio ω-6/ω-3 fatty acids (C 20 and higher) in the present product is preferably below 0.3, more preferably below 0.15, e.g. down to 0.03 or to 0.06.

An amount per day as described herein means an amount in a daily dosage unit provided by the composition of the invention. Such a daily dosage unit may be a single dosage, but it may also be divided over two or three, or even more daily servings. If the composition, as according to a preferred embodiment, is intended for administration as a single unit, the amounts per day as described herein, are preferably the amounts present in the (preferably packaged) composition unit. Treatment preferably involves administration once, twice or three times per day, more preferably once per day for a period of at least 3 weeks.

The present composition preferably comprises 1-40 wt. % DHA based on total fatty acids, preferably 3-36 wt. % DHA based on total fatty acids, more preferably 10-30 wt. % DHA based on total fatty acids. The present composition preferably comprises 0.5-20 wt. % EPA based on total fatty acids, preferably 2-10 wt. % EPA based on total fatty acids, more preferably 5-10 wt. % EPA based on total fatty acids. The above-mentioned amounts take into account and optimise several aspects, including taste (e.g. too high LCP levels reduce taste, resulting in a reduced compliance).

The present composition preferably contains at least one oil selected from fish oil, algae oil and eggs lipids. Preferably the present composition contains fish oil comprising DHA and EPA.

Saturated and Monounsaturated Fatty Acids

The present composition preferably comprises saturated and/or mono-unsaturated fatty acids. The amount of saturated fatty acids is preferably 6-60 wt. % based on total fatty acids, preferably 12-40 wt. %, more preferably 20-40 wt. % based on total fatty acids. In particular the amount of C14:0 (myristic acid)+C16:0 (palmitic acid) is preferably 5-50 wt. %, preferably 8-36, more preferably 15-30 wt. % wt. % based on total fatty acids. The total amount of monounsaturated fatty acids, such as oleic acid and palmitoleic acid, is preferably between 5 and 40 wt. %, more preferably between 15 and 30 wt. %. A composition with these preferred amounts was found to be very effective.

Phospholipids

Preferably, the present composition preferably comprises phospholipids, preferably 0.1-50 wt. % phospholipids based on total weight of lipids, more preferably 0.5-20 wt. %, more preferably between 1 and 10% wt. %, most preferably between 1 and 5 wt. % based on total weight of lipids. The total amount of lipids is preferably between 10 and 30 wt. % on dry matter, and/or between 2 and 10 g lipid per 100 ml for a liquid composition. The composition preferably comprises between 0.01 and 1 gram lecithin per 100 ml, more preferably between 0.05 and 0.5 gram lecithin per 100 ml. A composition with these preferred amounts was found to be very effective.

Choline

Preferably the present composition contains choline and/or phosphatidylcholine. The present method preferably comprises the administration of more than 50 mg choline per day, preferably 80-2000 mg choline per day, more preferably 120-1000 mg choline per day, most preferably 150-600 mg choline per day. The present composition preferably comprises 50 mg to 3 gram choline per 100 ml of the liquid formula, preferably 200 mg-1000 mg choline/100 ml.

Vitamins

The composition may advantageously contain vitamins, preferably vitamin C, vitamin E and B vitamins, more preferably vitamin C, vitamin E, vitamin B6, vitamin B12 and folic acid. Advantageously, vitamin B12 and folate are included. The present composition preferably comprises 50-1000 µg folic acid, more preferably 150-750 µg, most preferably 200-500 µg folic acid, per 100 ml liquid product. The present method preferably comprises the administration of 50-1000 µg folic acid per day, more preferably 150-750 µg, most preferably 200-500 µg folic acid per day. The present composition preferably comprises 0.5-15 µg vitamin B12, more preferably 1-10 µg, most preferably 1.5-5 µg vitamin B12, per 100 ml liquid product. The present method preferably comprises the administration 0.5-15 µg vitamin B12 per day, more preferably 1-10 µg, most preferably 1.5-5 µg vitamin B12 per day.

Preferably the present composition comprises one or more of phospholipids, choline, vitamin E, vitamin C, selenium, vitamin B12, vitamin B6 and folic acid, more preferably phospholipids, choline, vitamin E, vitamin C, selenium, vitamin B12, vitamin B6 and folic acid.

Product

The present composition is preferably a ready-to-use liquid, solid, or semi-liquid product. The present composition is preferably enterally administered, more preferably orally. Most preferably the present composition is administered through a straw. When it is a ready-to-use liquid, the daily liquid amount is preferably between 75 and 200 ml per day or per unit, most preferably between 90 and 150 ml/day.

The subjects that can benefit from the method and composition of the invention often experience problems with eating. Their sensory capabilities and/or control of muscles can become imparted, as well as in some instances their ambition to apply proper eating habits. Swallowing and/or mastication may be problematic. Hence, the present composition is preferably provided in the form of a drink capable of being ingested through a straw.

The composition according to the invention preferably has a low viscosity, preferably a viscosity between 1 and 2000 mPa·s measured at a shear rate of 100 sec$^{-1}$ at 20° C., more preferably a viscosity between 1 and 100 mPa·s measured at a shear rate of 100 sec$^{-1}$ at 20° C. More preferably, the present composition is provided in the form of a drink capable of being ingested through a straw which makes the product even easier to ingest and improves compliance. In a preferred embodiment the present composition has a viscosity of 1-80 mPas at a shear rate of 100 per sec at 20° C., more preferably of 1-40 mPas at a shear rate of 100 per sec at 20° C. These viscosity measurements may for instance be performed using plate and cone geometry.

To be optimally accepted by the subject, the present composition preferably has an osmolality of 300 to 800 mOsm/kg. However, the energy density of the product is preferably not so high that it interferes with normal eating habits. When in liquid form, the present product preferably contains between 0.2 and 3 kcal/ml, more preferably between 0.5 and 2, between 0.7 and 1.5 kcal/ml.

Advantageously the present composition contains digestible carbohydrates. The present composition preferably contains between 1 and 50 gram digestible carbohydrates per 100 ml of a liquid product, more preferably between 5 and 30 grams per 100 ml, more preferably 10-30 grams carbohydrates per 100 ml. The total amount of digestible carbohydrates is preferably between 25 and 80 wt. % on dry matter, preferably 40-80 wt. % based on dry matter.

The present composition may further comprise protein, preferably 0.5-10 g protein per 100 ml, more preferably 1-6 gram protein per 100 ml, most preferably 2-6 gram protein/ 100 ml. Preferably the present composition contain at least 80 wt. % milk derived protein (e.g. whey and/or casein) based on total protein. Proteins enable the manufacturing of palatable products, especially for frail elderly.

EXAMPLES

Example 1

Packaged composition for the comprising per 125 ml:
Energy 125 kcal; Protein 3.9 g; Carbohydrate 16.5 g; Fat 4.9 g.
Fat includes 1.5 g DHA+EPA, and 106 mg phospholipids (soy lecithin); Choline 400 mg; UMP (uridine monophosphate) 625 mg; Vitamin E 40 mg α-TE; Vitamin C 80 mg; Selenium 60 µg; Vitamin B12 3 µg; Vitamin B6 1 mg; Folic acid 400 µg.
Minerals and trace elements: Sodium 125 mg; Potassium 187.5 mg; Chloride 156.3 mg; Calcium 100 mg; Phosphorus 87.5 mg; Magnesium 25 mg; Iron 2 mg; Zinc 1.5 mg; Copper 225 µg; Manganese 0.41 mg; Molybdenum 12.5 µg; Chromium 8.4 µg; Iodine 16.3 µg. Vitamins: Vit. A 200 µg-RE; vit. D3 0.9 µg; vit. K 6.6 µg; Thiamin (B1) 0.19 mg; Riboflavin (B2) 0.2 mg; Niacin (B3) 2.25 mg-NE; Pantothenic acid (B5) 0.66 mg; Biotin 5 µg.

Example 2: Clinical Study

Increasing evidence shows a role of nutrients in subjects with impaired memory function. The present study was done to assess the effect of an intervention with a medical food on memory in drug naïve, very mild Alzheimer's disease (AD) subjects. Drug naïve very mild AD subjects with a MMSE of 24-26 were randomly allocated in a double-blind 12 weeks study to receive a 125 ml (125 kcal) once-a-day milk-based drink with: (a) the formula according to example 1 (active product) or (b) an iso-caloric control drink according to example 1, but without EPA, DHA, phospholipids, choline, UMP, vitamin E, vitamin C, selenium, vitamin B12, vitamin B6 and folic acid (control product).

Outcome measure was a (delayed) verbal memory task (derived from Wechsler Memory Scale-revised).

Results:

At baseline, there was no significant difference between the group treated with the active product and the group treated with the control product. However, there was a significant difference between the two groups in the change in the delayed verbal memory task (derived from Wechsler Memory scale-revised (WMS-r)) between baseline and after 12 weeks of treatment. The group receiving control product (n=66) had an average decline of −0.164 with a 95% confidence interval including zero (−0.938 to 0.610) whereas the group receiving active product (n=60) had an average improvement of 0.983 points on the delayed verbal memory scale derived from WMS-r with a 95% confidence interval above zero (0.214 to 1.752).

This study demonstrates that intervention with the active product for 12 weeks improves memory, particularly delayed recall function in subjects with MMSE of 24-26 (see Table 1).

TABLE 1

| Group | Subjects with MMSE 24-26 | Delayed verbal memory score (WMS-r) |
|---|---|---|
| Control | 66 | −0.164 |
| Treatment | 60 | +0.983 |

The invention claimed is:

1. An enteral composition comprising:
   a. uridine or uridine phosphate;
   b. docosahexaenoic acid;
   c. eicosapentaenoic acid;
   d. phospholipids;
   e. choline;
   f. vitamin E;
   g. vitamin C;
   h. selenium;
   i. vitamin B12;
   j. vitamin B6; and
   k. folic acid.

2. The composition according to claim 1, comprising, per daily dosage unit:
   0.1-2 g uridine, calculated as uridine monophosphate, wherein uridine is the cumulative amount of uridine, deoxyuridine, uridine phosphates, uracil and acylated uridine derivatives,
   400-5000 mg of the sum of DHA and EPA,
   80-2000 mg choline,
   50-1000 μg folic acid,
   0.5-15 μg vitamin B12.

3. The composition according to claim 1, comprising 0.1-2 g uridine, calculated as uridine monophosphate, per daily dosage unit.

4. The composition according to claim 1, comprising 400-5000 mg of the sum of DHA and EPA per daily dosage unit.

5. The composition according to claim 3, comprising 400-5000 mg of the sum of DHA and EPA per daily dosage unit.

6. The composition according to claim 1, comprising 1-50 gram digestible carbohydrates per 100 ml.

7. The composition according to claim 1, comprising 0.5-10 g protein per 100 ml.

8. The composition according to claim 1, comprising 0.2-3 kcal/ml.

9. The composition according to claim 1, comprising 1-50 gram digestible carbohydrates per 100 ml, 0.5-10 g protein per 100 ml, and 0.2-3 kcal/ml.

10. The composition according to claim 1, being a liquid product, having a viscosity between 1 and 100 mPa·s as measured at a shear rate of 100 s−1 at 20° C.

* * * * *